(12) United States Patent
Yen et al.

(10) Patent No.: US 7,282,586 B1
(45) Date of Patent: Oct. 16, 2007

(54) DIPYRIDINE-BASED COMPOUND AND THE USE THEREOF

(75) Inventors: Feng-Wen Yen, Hsinchu (TW); Chao-Yu Chiu, Hsinchu (TW); I-Feng Lin, Taoyuan (TW); Chin-Ming Teng, Miaoli County (TW); Pei-Chi Yen, Hsinchu (TW)

(73) Assignee: Luminescence Technology Corp., Hsinchu (TW)

( * ) Notice: Subject to any disclaimer, the term of this patent is extended or adjusted under 35 U.S.C. 154(b) by 3 days.

(21) Appl. No.: 11/464,190

(22) Filed: Aug. 11, 2006

(51) Int. Cl.
*C07D 471/02* (2006.01)
*H05B 33/12* (2006.01)

(52) U.S. Cl. .................. 546/88; 428/917; 428/690; 546/15; 544/343; 313/504; 313/506

(58) Field of Classification Search .............. 546/15, 546/88; 544/343; 428/917, 690; 313/504, 313/506
See application file for complete search history.

(56) References Cited

OTHER PUBLICATIONS

Wong, K-T. et al,: Novel spiro-configured PET chromophores incorporating 4,5-diazafluorene moiety as an electron acceptor. Organic letters, vol. 8, pp. 3501-3504, 2006.*

* cited by examiner

*Primary Examiner*—Charanjit S. Aulakh
(74) *Attorney, Agent, or Firm*—WPAT, P.C.; Justin I. King

(57) ABSTRACT

The present invention discloses a dipyridine-based compound which can be used as electron-transporting and/or hole blocking material or phosphorous host in organic electroluminescence devices is disclosed. The mentioned dipyridine-based compound is represented by the following formula:

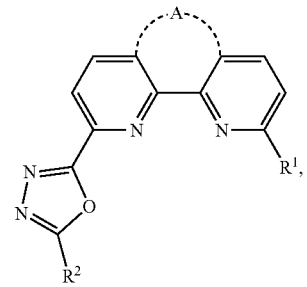

wherein $R^1$ and $R^2$ are identical or different, and $R^1$ and $R^2$ are independently selected from the group consisting of: hydrogen atom, aryl moiety, hetero cycle, multiple fused ring, multiple fused ring with hetero atom(s); A is selected from the following group:

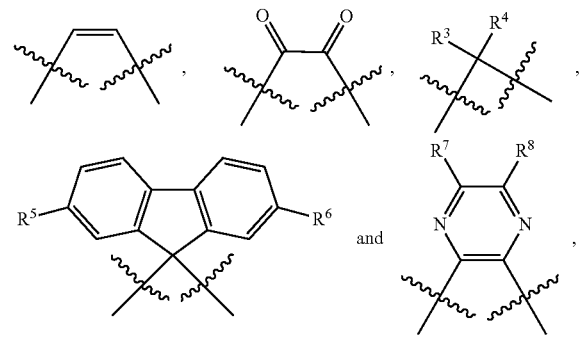

wherein $R^3$ and $R^4$ are identical or different, $R^5$ and $R^6$ are identical or different, $R^7$ and $R^8$ are identical or different, $R^3$, $R^4$, $R^7$, $R^8$ are independently selected from the group consisting of: alkyl moiety and aryl moiety, and $R^5$, $R^6$ are independently selected from the group consisting of: alkyl moiety, aryl moiety and arylamine moiety.

17 Claims, 5 Drawing Sheets

Device 1-1:
ITO/LT-N121(400 Å)/CBP doped 10%Ir(piq)$_2$acac(300 Å)/
BCP(100 Å)/Alq$_3$(200 Å)/LiF(5 Å)/Al(1200 Å)
Device 1-2:
ITO/LT-N121(400 Å)/CBP doped 10%Ir(piq)$_2$acac(300 Å)/
compound 2(100 Å)/Alq$_3$(200 Å)/LiF(5 Å)/Al(1200 Å)

Device 2-1:
ITO/NPB(500 Å)/Alq$_3$(600 Å)/LiF(5 Å)/Al(1200 Å)
Device 2-2:
ITO/NPB(500 Å)/Alq$_3$(200 Å)/compound 8(400 Å)/LiF(5 Å)/Al(1200 Å)

DIPYRIDINE-BASED COMPOUND AND THE USE THEREOF

BACKGROUND OF THE INVENTION

1. Field of the Invention

The present invention is generally related to dipyridine-based compounds, and more particularly to dipyridine-based compounds and their use as electron-transporting and/or hole blocking materials or phosphorous host.

2. Description of the Prior Art

Organic light-emitting devices (OLEDs) have received much attention due to their potential applications to flat panel displays. OLEDs are generally composed of functionally divided organic multi-layers, e.g., hole transporting (HT), emissive, and electron transporting (ET) layers, and so on. In the last decade, many kinds of amorphous molecular semiconductor materials, working as HT materials and ET materials, have been proposed, and HT molecular semiconducting materials have become practical due to their high charge carrier mobility and excellent operational durability. On the other hand, there have been few reports of ET organic semiconducting amorphous materials with high performance (high-speed transportation of electrons, easy injection of electrons from the cathode, and good operational durability).

Efficient ET materials provide some advantages, such as lowering the operating voltage and power consumption. Moreover, if the ET materials have wide band gaps, in other words, deeper highest occupied molecular orbitals (HOMO), such ET materials can also work as hole blocking (HB) materials. The complete confinement of a hole in an emissive layer by the HB layer raises the quantum efficiencies of electroluminescence (EL). Oxadiazole is a well-known electron accepting component for building ET materials with high electron mobility, and oxadiazole derivatives (OXDs) exhibit wide band gap properties because oxadiazole restricts extensions of p-conjugation beyond the ring even if the molecule is co-planar. Accordingly, OXDs are a promising ET and HB material for OLEDs, but it has been widely accepted that OXDs should acquire durability capacity for long-term operations in OLEDs. Therefore, new electron-transporting and/or hole blocking materials are still needed corresponding to increasing thermal stability and practical operation durability.

SUMMARY OF THE INVENTION

In accordance with the present invention, new dipyridine-based compounds and their use are provided. These new dipyridine-based compounds can overcome the drawbacks of the mentioned conventional materials.

In order to obtain better thermal stability, we introduced a steric bridge moiety to further connect two pyridine moieties, so as to form the dipyridine-based compounds. Therefore, steric effect and the enlargement of molecular size enhances the stability of the amorphous glassy state.

One object of the present invention is to employ dipyridine-based structure as core structure. It is well accepted that pyridine is an electron-deficient heterocycle. Therefore, by combining pyridine and other electron-deficient units (i.e. oxadiazoles) in the same molecule, we can improve the hole-blocking and/or electron-transporting properties of these materials.

Another object of the present invention is to introduce a steric bridge moiety to connect two pyridine moieties, so as to form the dipyridine-based compounds. By applying this strategy, this invention provides a novel series of dipyridine-based compounds, which have better thermal stability in comparison with the corresponding oxadiazole derivatives. Steric effect and the enlargement of molecular size of the mentioned dipyridine-based compounds enhance the stability of the amorphous glassy state. Therefore, this present invention does have the economic advantages for industrial applications.

Accordingly, the present invention discloses a dipyridine-based compound which can be used as electron-transporting and/or hole blocking material or phosphorous host in organic electroluminescence devices is disclosed. The mentioned dipyridine-based compound is represented by the following formula:

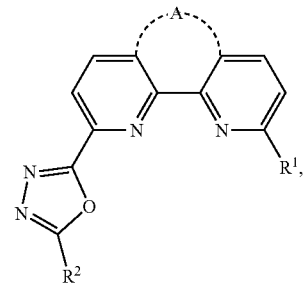

wherein $R^1$ and $R^2$ are identical or different, and $R^1$ and $R^2$ are independently selected from the group consisting of: hydrogen atom, aryl moiety, hetero cycle, multiple fused ring, multiple fused ring with hetero atom(s); A is selected from the following group:

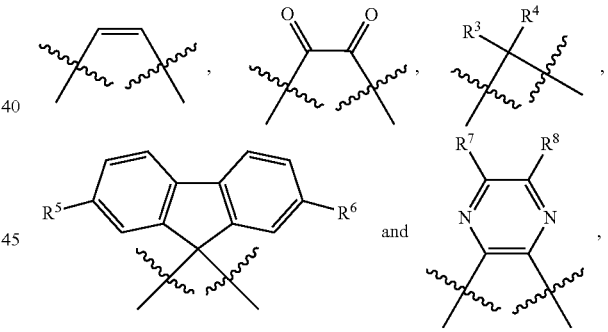

wherein $R^3$ and $R^4$ are identical or different, $R^5$ and $R^6$ are identical or different, $R^7$ and $R^8$ are identical or different, $R^3$, $R^4$, $R^7$, $R^8$ are independently selected from the group consisting of: alkyl moiety and aryl moiety, and $R^5$, $R^6$ are independently selected from the group consisting of: alkyl moiety, aryl moiety and arylamine moiety.

DESCRIPTION OF THE PREFERRED EMBODIMENTS

Figure 1A:
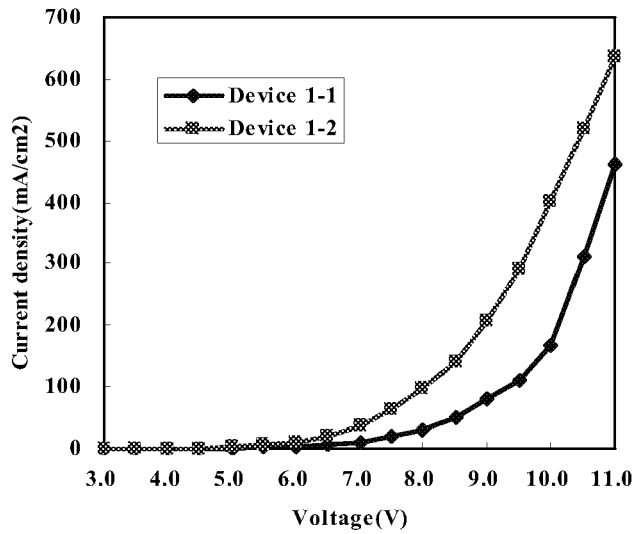
FIG. 1A shows plots of current density v. voltage for device 1-1 and device 1-2.

What probed into the invention are dipyridine-based compounds and the use thereof. Detailed descriptions of the production, structure and elements will be provided in the following in order to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now by described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Definition

The term "thermal degradation temperature ($T_d$)" herein refers to the temperature when the weight loss of a heated specimen being 0.5 wt %.

In a first embodiment of the present invention, a dipyridine-based compound which can be used as electron-transporting and/or hole blocking material or phosphorous host in organic electroluminescence devices is disclosed. The mentioned dipyridine-based compound is represented by the following formula:

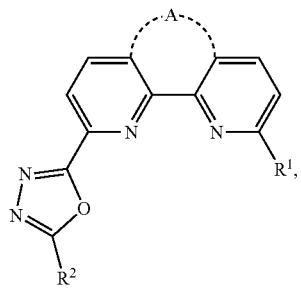

wherein $R^1$ and $R^2$ are identical or different, and $R^1$ and $R^2$ are independently selected from the group consisting of: hydrogen atom, aryl moiety, hetero cycle, multiple fused ring, multiple fused ring with hetero atom(s); A is selected from the following group:

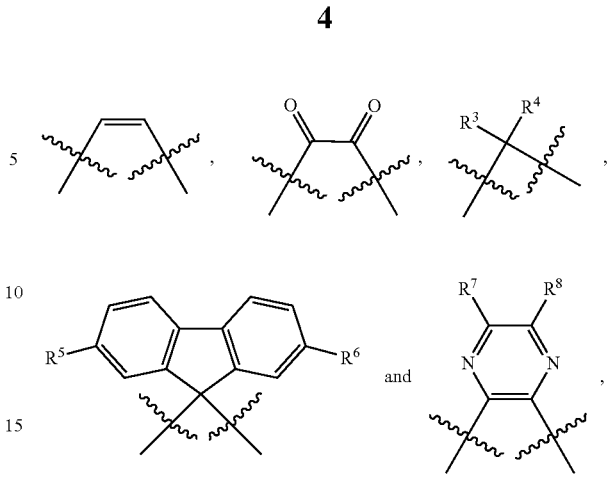

wherein $R^3$ and $R^4$ are identical or different, $R^5$ and $R^6$ are identical or different, $R^7$ and $R^8$ are identical or different, $R^3$, $R^4$, $R^7$, $R^8$ are independently selected from the group consisting of: alkyl moiety and aryl moiety, and $R^5$, $R^6$ are independently selected from the group consisting of: alkyl moiety, aryl moiety and arylamine moiety.

In this embodiment, $R^1$ comprises one of the following groups:

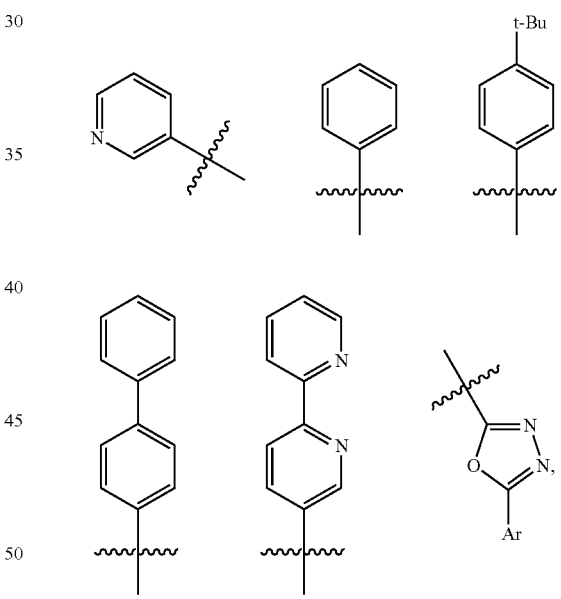

wherein Ar is aryl moiety. Furthermore, $R^2$ comprises one of the following groups:

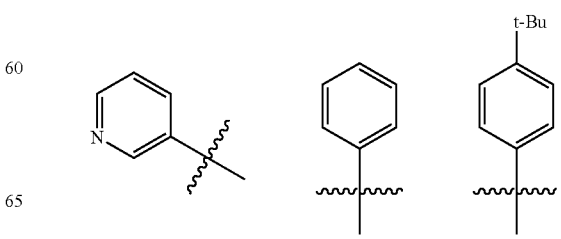

-continued
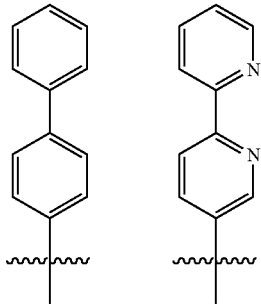
Moreover, $R^5$ and $R^6$ comprises one of the following groups:
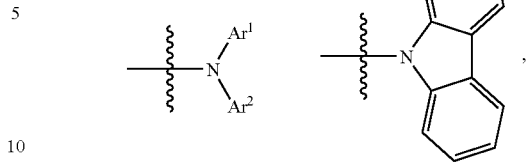
wherein $Ar^1$ and $Ar^2$ are identical or different, $Ar^1$ and $Ar^2$ are aryl moieties.
In this embodiment, some dipyridine-based compounds are listed in Table 1.
| Structure formula |
|---|
| Compound 1 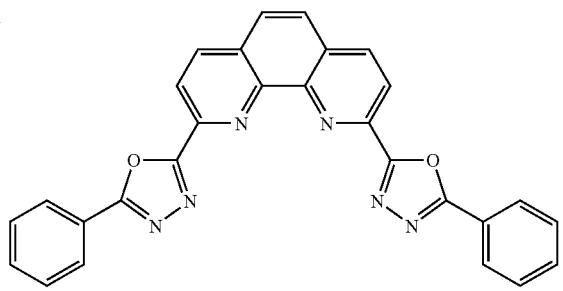 |
| Compound 2 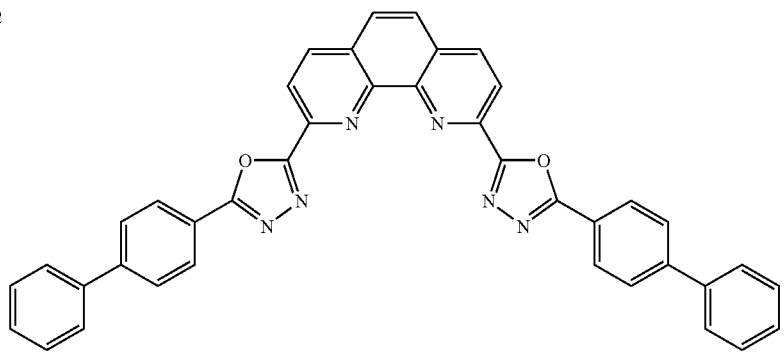 |
| Compound 3 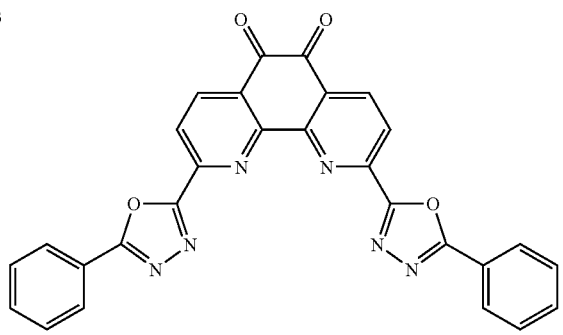 |

-continued

| Structure formula |
|---|
| Compound 4 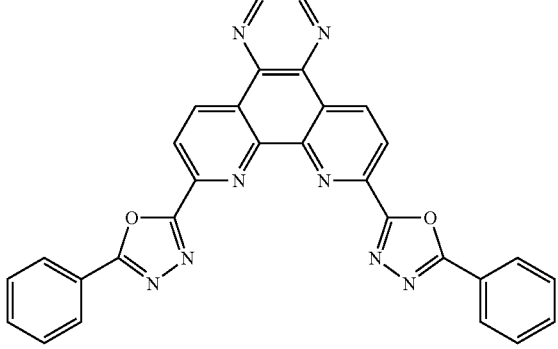 |
| Compound 5 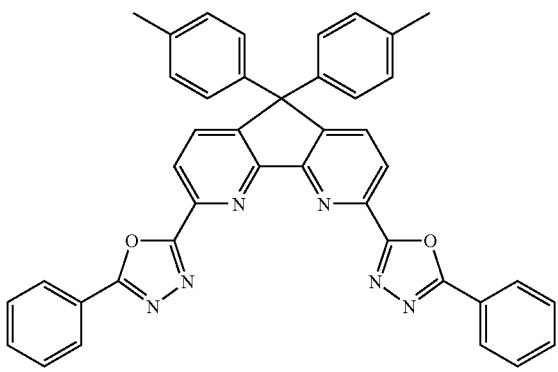 |
| Compound 6 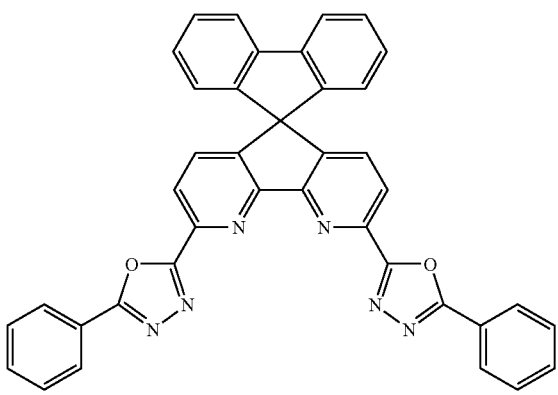 |

EXAMPLE 1

Synthesis of Compound 1

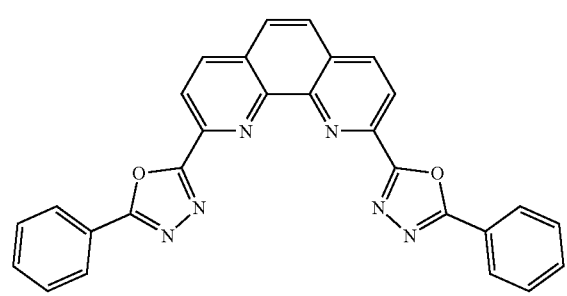

Step 1

Referring to Scheme 1, under nitrogen atmosphere, a mixture of 50 g (0.277 mol) [1,10]phenanthroline, 133.5 g (1.37 mol) 35% hydrogen peroxide and 300 ml acetic acid was added to a 500 ml one-necked flask. The mixture was then stirred overnight at 70° C. After completion of the reaction, the reaction mixture was vacuum concentrated to reduce acetic acid to 30 ml, and 300 ml methanol was then added to give solids. Finally, the solids were washed by acetone to give [1,10]phenanthroline N,N'-dioxide 34 g (0.16 ml, yield 57%).

Step 2

To a 2 L beaker was added a mixture of 34 g (0.16 mol) [1,10]phenanthroline N,N'-dioxide, 64.37 g (0.99 mol) potassium cyanide and 700 ml water, and the mixture was then stirred till becoming homogeneous. Next, 78.2 g (0.55 mol) benzoyl chloride was added into the mixture drop by drop to obtain solids. After the adding, the reaction mixture was stirred for 15 minutes. Finally, solids were separated, washed by 100 ml ethanol, filtered and dried to give [1,10] phenanthroline 2,9-dicarbonitrile 26 g (0.112 mol, yield 70%).

Step 3

Under nitrogen atmosphere, a mixture of 26 g [1,10] phenanthroline 2,9-dicarbonitrile (0.11 mol), 18.9 g (0.29 mol) sodium azide, 15.6 g (0.29 mol) ammonium chloride, 0.27 g (0.006 mol) lithium chloride and 260 ml DMF was added to a 500 ml one-necked flask. The mixture was then heated to reflux (130° C.) and stirred overnight. After completion of reaction, the reaction mixture was cooled to room temperature, filtered, and vacuum distillated to reduce DMF to 50 ml, and 300 ml water was then added. Next, 37% HCl was added drop by drop to adjust the pH value to a range from 3 to 4, and then stirred for 30 minutes. Finally, solids were separated, washed by 150 ml methanol, filtered and dried to give white 2,9-bis-(1H-tetrazol-5-yl)-[1,10] phenanthroline 13 g (0.045 mol, yield 40%).

Step 4

Under nitrogen atmosphere, a mixture of 13 g (0.045 mol) 2,9-bis-(1H-tetrazol-5-yl)-[1,10]phenanthroline and 390 ml pyridine was added to a 250 ml three-necked flask. The mixture was then heated to 50° C., and 24.6 g (0.17 mol) benzoyl chloride was then added drop by drop. After the adding, the mixture solution was heated to reflux (110° C.) and stirred overnight. After completion of reaction, the reaction mixture was cooled to room temperature, filtered. Finally, solids were separated, washed by 100 ml methanol, filtered and purified by column chromatography to obtain white products 2,9-bis-(5-phenyl-[1,3,4]oxadiazol-2-yl)-[1,10]phenanthroline 4 g (0.008 mol, yield 17%). MS(m/z, FAB$^+$), 468, 467, 307, 154, 105.

Scheme 1

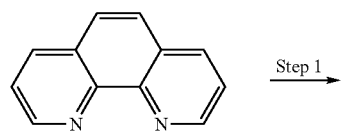

Step 1

-continued

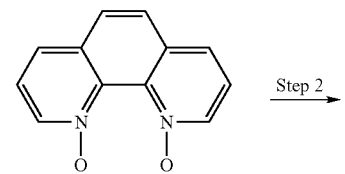

Step 2

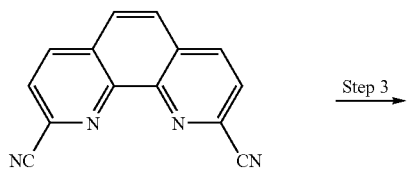

Step 3

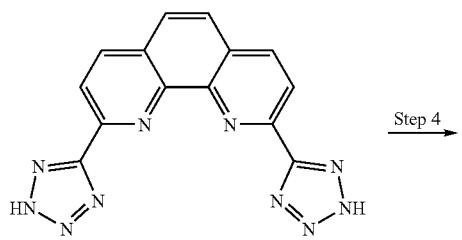

Step 4

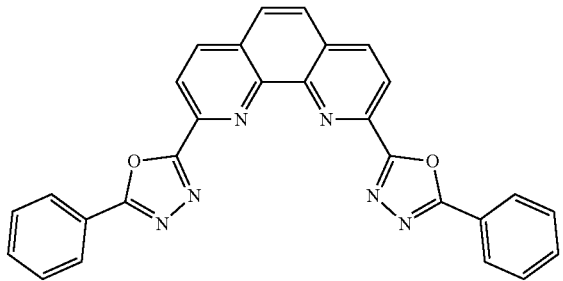

EXAMPLE 2

Synthesis of Compound 2

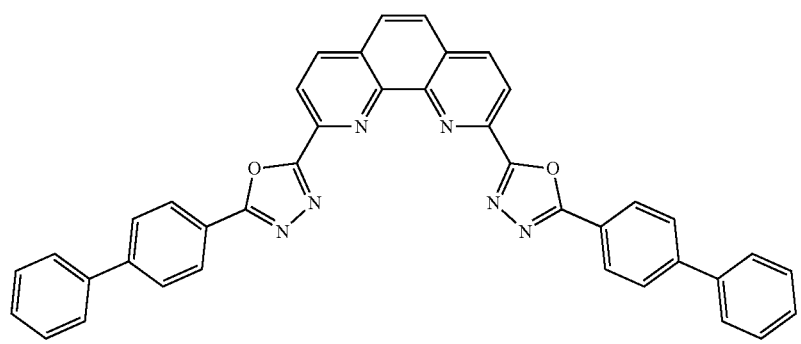

Under nitrogen atmosphere, a mixture of 13 g (0.045 mol) 2,9-bis-(1H-tetrazol-5-yl)-[1,10]phenanthroline and 390 ml pyridine was added to a 250 ml three-necked flask. The mixture was then heated to 50° C., and 46 g (0.21 mol) 4-phenylbenzoyl chloride was then added drop by drop. After the adding, the mixture solution was heated to reflux (110° C.) and stirred overnight. After completion of reaction, as shown in scheme 2, the reaction mixture was cooled to room temperature, filtered. Finally, solids were separated, washed by 100 ml methanol, filtered and purified by column chromatography to obtain white products 2,9-bis-(5-biphenyl-4-yl-[1,3,4]oxadiazol-2-yl)-[1,10]phenanthroline 11 g (0.018 mol, yield 40%). MS(m/z, FAB$^+$), 620, 291, 248, 233, 208, 156, 130, 105.

10]phenanthroline and 15.3 ml sulfuric acid (concentrate). The mixture was subsequently iced and 15.3 ml HNO$_3$ was added into the iced mixture drop by drop. Next, 1.5 g (0.013 mol) potassium bromide was added to the iced mixture, and then the mixture solution was heated to 40° C. and stirred overnight. After completion of reaction, as shown in Scheme 3, the reaction mixture was placed into 200 ml iced water, and then NaOH$_{(aq)}$ was added to adjust pH value to a range from 5 to 6. Next, 150 ml CH$_2$Cl$_2$ was subsequently added. The organic layer was separated, dehydrated by MgSO$_4$, concentrated, and purified by column chromatography to obtain white products 2,9-bis-(5-phenyl-[1,3,4]oxadiazol-2-yl)-[1,10]phenanthroline-5,6-dione 0.8 g (0.0016 mol, yield 20%).

Scheme 2

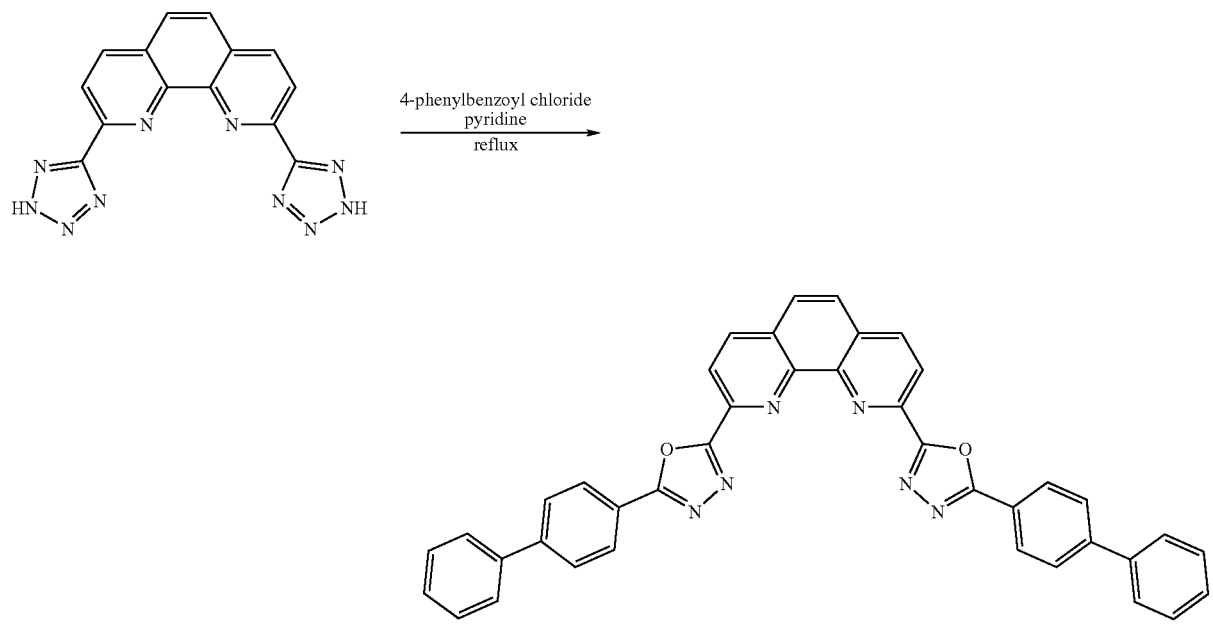

EXAMPLE 3

Synthesis of Compound 3

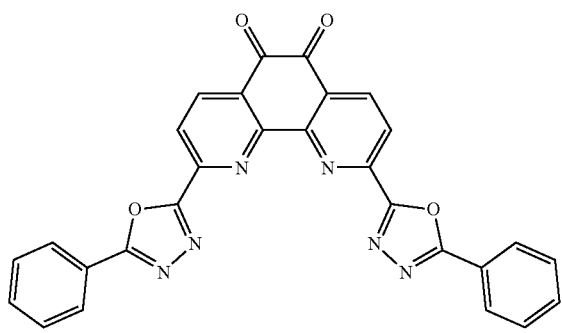

Scheme 3

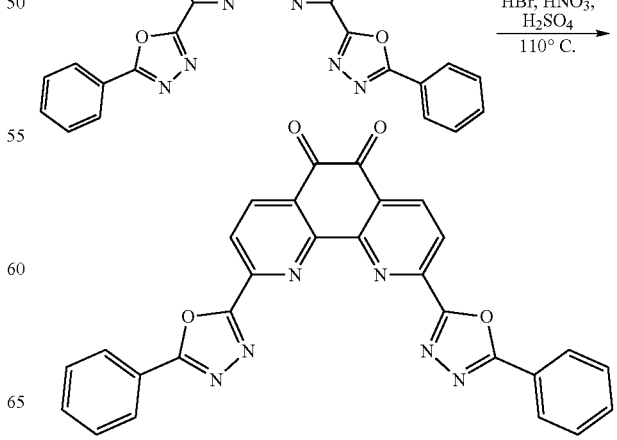

To a 100 ml one-necked flask was added a mixture of 4 g (0.008 mol) 2,9-bis-(5-phenyl-[1,3,4]oxadiazol-2-yl)-[1,

EXAMPLE 4

Synthesis of Compound 4

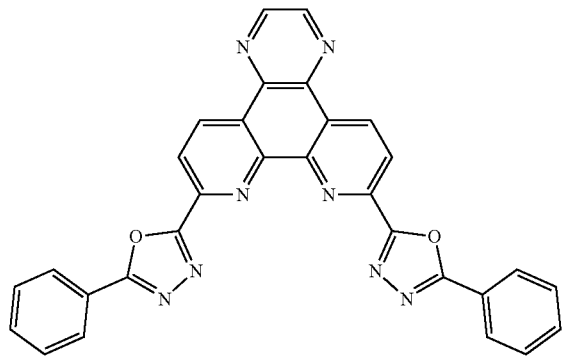

To a 100 ml one-necked flask was added a mixture of 17 g (0.08 mol) 2,9-bis-(5-phenyl-[1,3,4]oxadiazol-2-yl)-[1,10]phenanthroline-5,6-dione, 8.84 g (0.08 mol) diaminoalenitrile and 50 ml acetice acid. Next, the mixture was heated to 110° C. and stirred overnight. After completion of reaction, as shown in Scheme 4, the reaction mixture was cooled to room temperature and filtered to obtain solids. The solids were washed subsequently by water and hexane, and then dried to obtain brown products 7,10-bis-(5-phenyl-[1,3,4]oxadiazol-2-yl)-1,4,8,9-tetraaza-triphenylene 22.1 g (0.078 mol, yield 98%). MS(m/z, FAB+), 520, 306, 154, 105.

Scheme 4

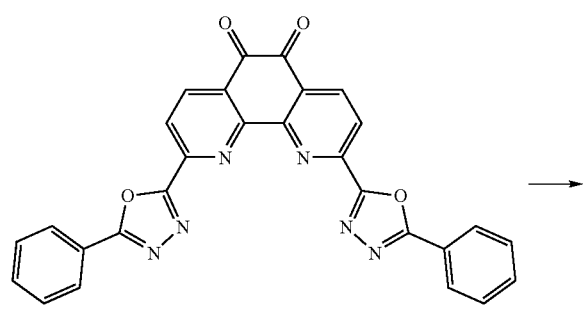

→

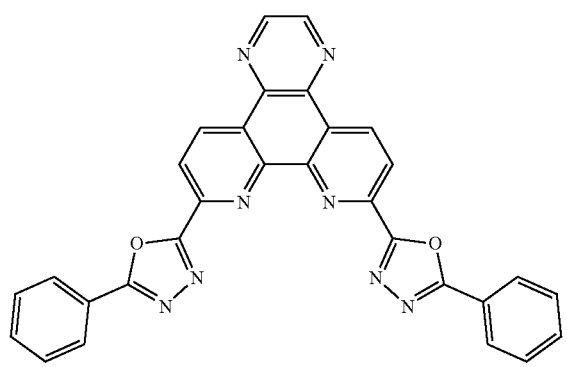

EXAMPLE 5

Synthesis of Compound 5

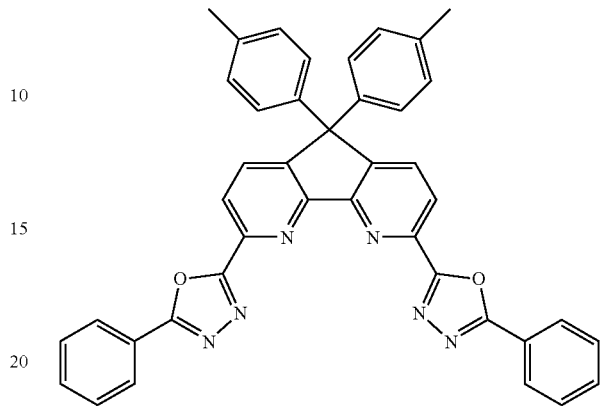

Step 1

Referring to Scheme 5, 237 ml sulfuric acid (concentrate) was first added to a 1 L three-necked flask. 35 g 1,10-phenanthroline was then added into the flask, and the temperature of mixture was kept lower than 100° C. Next, 2436 ml (67%) HNO$_3$ was added drop by drop, and the temperature of mixture was kept lower than 110° C. The mixture was subsequently heated to 100° C. and stirred overnight. After completion of reaction, the reaction mixture was cooled to room temperature and placed into 2 L water, and then NaOH$_{(aq)}$ was added to adjust pH value to a range from 6 to 7, so as to give solids. The solids were washed by water, and dried to obtain solids 5-nitro-1,10-phenanthroline 30 g (0.13 mol, yield 68%).

Step 2

To a 1 L one-necked flask was added a mixture of 30 g (0.13 mol, 68%) 5-nitro-1,10-phenanthroline, 51 g (0.61 mol) potassium oxalate, 12.5% NaOH$_{(aq)}$ 150 ml and 450 ml water. The mixture was then heated to reflux (100° C.) and stirred for 2 hours. After completion of the reaction, the reaction mixture was cooled to room temperature. The reaction mixture was added with 1 L ethyl acetate, stirred for 30 minutes, and filtered to collect the filtrate. The residual solids were added into 300 ml ethyl acetate, stirred for 30 minutes and filtered to collect the filtrate. The combined filtrates were extracted to separate the organic layer, dehydrated by MgSO$_4$, concentrated, and recrystallized from 200 ml methanol, so as to obtain light yellow solids cyclopenta[2,1-b;3,4-b']dipyridin-5-one 13.3 g (0.07 mol, yield 54%).

Step 3

To a 500 ml one-necked flask was added a mixture of 13.3 g (0.07 mol) cyclopenta[2,1-b;3,4-b']dipyridin-5-one 134.3 g (1.4 mol) tolune and 137.2 g (1.4 mol) sulfuric acid (concentrate). The mixture was then heated to reflux (110° C.) and stirred for 48 hours. After completion of reaction, the reaction mixture was placed into 500 ml water and stirred for 30 minutes to give solids. The solids were then washed by water and dried to obtain white solids 5,5-di-p-toyl-5H-cyclopenta[2,1-b;3,4-b']dipyridine 8 g (0.023 mol, yield 32%).

Step 4

Under nitrogen atmosphere, a mixture of 8 g (0.023 mol) 5,5-di-p-toyl-5H-cyclopenta[2,1-b;3,4-b']dipyridine, 11.7 g (0.115 mol) 35% hydrogen peroxide and 78 ml acetic acid was added to a 250 ml one-necked flask. The mixture was then heated to 70° C. and stirred overnight. After completion of reaction, the reaction mixture was vacuum concentrated, and added with 100 ml $CH_2Cl_2$ and 100 ml water respectively. The adding process was repeated one more time. Finally, the organic layer was separated, dehydrated by $MgSO_4$ and vacuum concentrated to obtain 5,5-di-p-toyl-5H-cyclopenta[2,1-b;3,4-b']dipyridine-N,N'-dioxide 8.32 g (0.021 mol, yield 95%).

Step 5

To a 500 ml beaker was added a mixture of 8.32 g (0.021 mol) 5,5-di-p-toyl-5H-cyclopenta[2,1-b;3,4-b']dipyridine-N,N'-dioxide, 4.1 g (0.063 mol) potassium cyanide and 200 ml water, and the mixture was then stirred till becoming homogeneous. Next, 8.86 g (0.063 mol) benzoyl chloride was added drop by drop to give solids. After the adding, the reaction mixture was stirred for 15 minutes, filtered and dried to obtain 5,5-di-p-toyl-5H-cyclopenta[2,1-b;3,4-b']dipyridine-2,8-dicarbonitrile 5.98 g (0.015 mol, yield 70%).

Step 6

Under nitrogen atmosphere, a mixture of (5,5-di-p-toyl-5H-cyclopenta[2,1-b;3,4-b']dipyridine-2,8-dicarbonitrile) 5.98 g (0.015 mol), 2.93 g (0.045 mol) sodium azide, 2.41 g (0.045 mol) ammonium chloride, 0.03 g (0.075 mmol) lithium chloride and 60 ml DMF was added to a 250 ml one-necked flask. The mixture was then heated to reflux (130° C.) and stirred overnight. After completion of reaction, the reaction mixture was cooled to room temperature and filtered. The filtrate vacuum distillated to reduce DMF to 50 ml, and 300 ml water was then added. Next, 37% HCl was added drop by drop to adjust the pH value to a range from 3 to 4, and then stirred for 30 minutes. Finally, solids were separated, washed by 150 ml methanol, filtered and dried to give white 2,8-bis-(2H-tetrazol-5-yl)-5,5-di-p-toyl-5H-cyclopenta[2,1-b;3,4-b']dipyridine 3.85 g (7.9 mol, yield 53%).

Step 7

Under nitrogen atmosphere, a mixture of 3.85 g (7.9 mmol), 2,8-bis-(2H-tetrazol-5-yl)-5,5-di-p-toyl-5H-cyclopenta[2,1-b;3,4-b']dipyridine and 115 ml pyridine was added to a 250 ml three-necked flask. The mixture was heated to 50° C., and 4.44 g (31.6 mmol) benzoyl chloride was added drop by drop. Next, the mixture solution was heated to reflux (110° C.) and stirred overnight. After completion of reaction, the reaction mixture was cooled to room temperature and filtered to collect solids. The solids was added into 100 ml methanol and stirred for 30 minutes, filtered, purified by column chromatography to obtain white products 2,8-bis-(5-phenyl-[1,3,4]oxadiazol-2-yl)-5,5-di-p-toyl-5H-cyclopenta[2,1-b;3,4-b']dipyridine 3.07 g (4.8 mmol, yield 61%). MS(m/z, $FAB^+$), 712, 248, 208, 181, 156.

Scheme 7

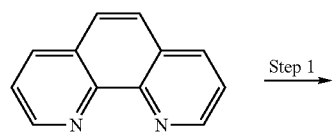

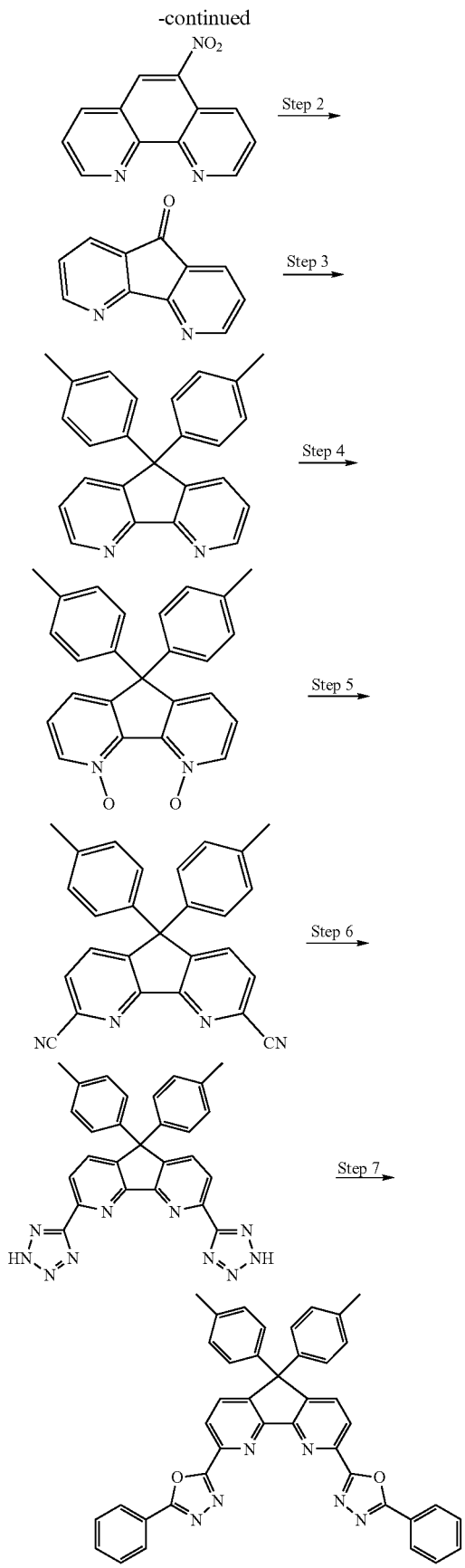

EXAMPLE 6

Synthesis of Compound 6

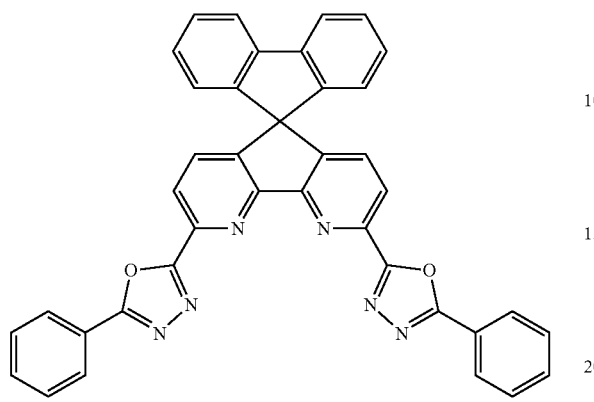

Step 1

Referring to scheme 6, under reflux, a flask containing with arylmagnesium iodide that was firstly prepared in advance from 2-iodo-biphenyl (11.2 g, 40 mmol) and magnesium (0.97 g, 40 mmol) in ether was added into 4,5-diazafluoren-9-one (3.64 g, 20 mmol) in THF. The mixture was refluxed for another 12 hours, then quenched with water after cooling to ambient temperature and extracted with CHCl$_3$. The combined organic extracts were dried (MgSO$_4$) and concentrated by rotary evaporation. The resulting crude solid was washed with n-hexane to give 5-biphenyl-2-yl-5H-cyclopenta[2,1-b;3,4-b']dipyridin-5-ol (6.3 g, 93% yield) as a light brown solid, which was used for cyclization without further purification. 5-biphenyl-2-yl-5H-cyclopenta[2,1-b;3,4-b']dipyridin-5-ol was heated to dissolve in 500 ml acetic acid. The solution was added 6 ml sulfuric acid as catalyst and refluxed for 24 hours. The reaction was quenched with cold water after cooling to room temperature and neutralized with NaOH(aq) to basic, then extracted with CHCl$_3$ and dried with MgSO$_4$. The combined organic solution was concentrated by rotary evaporation and washed with n-hexane to give 4,5-diaza-9,9'-spirobifluorene (4.3 g, 75%) as a light brown solid.

Step 2 to Step 5: Similar to Step 4 to Step 7 in Example 5

Scheme 6

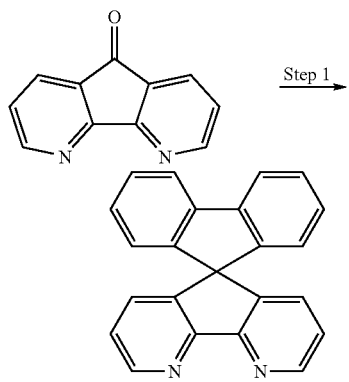

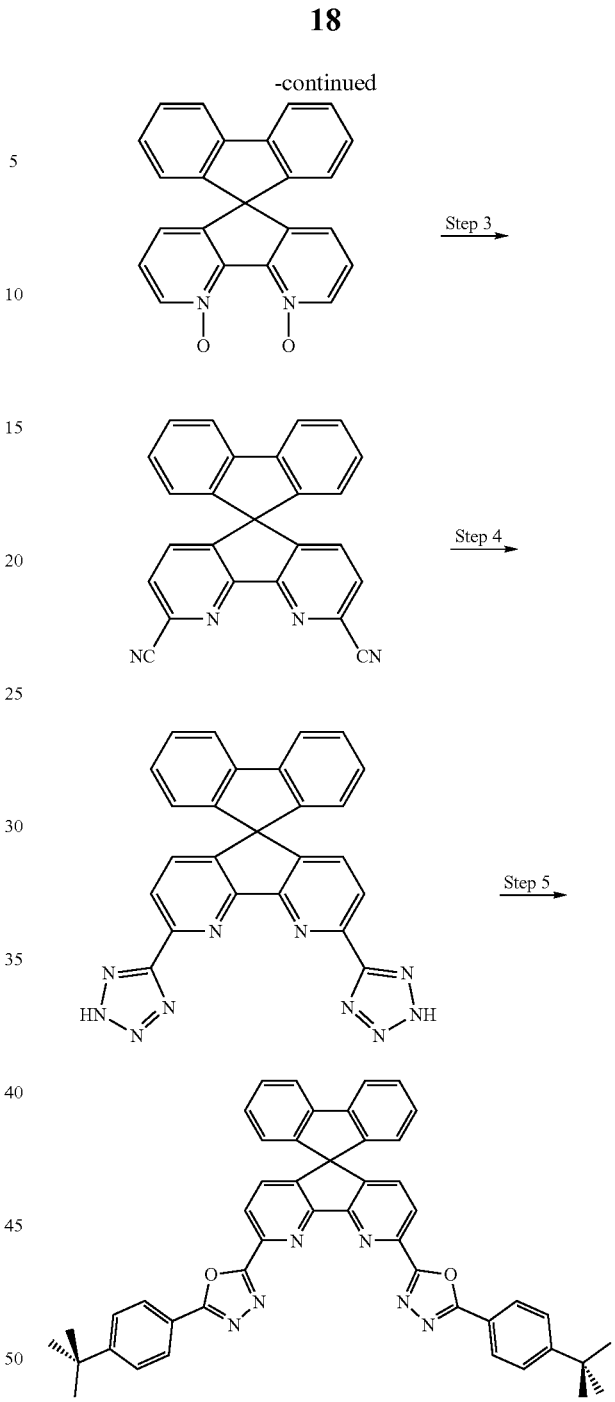

In a second embodiment of the present invention, a dipyridine-based compound which can be used as electron-transporting and/or hole blocking material or phosphorous host in organic electroluminescence devices is disclosed. The mentioned dipyridine-based compound is represented by the following formula:

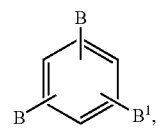

wherein B¹=B or hydrogen atom, and the structure of B is as following:

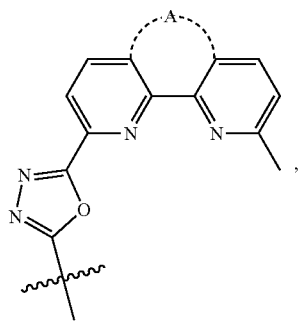

wherein A is selected from the following group:

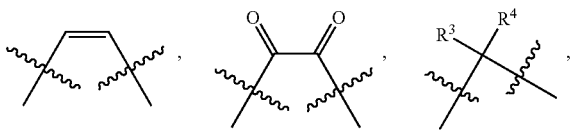

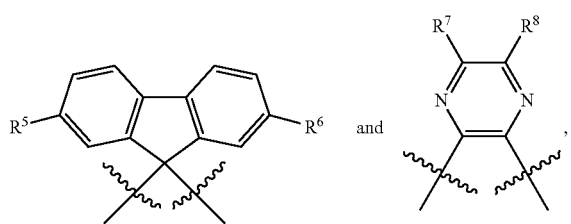

wherein R³ and R⁴ are identical or different, R⁵ and R⁶ are identical or different, R⁷ and R⁸ are identical or different, R³, R⁴, R⁷, R⁸ are independently selected from the group consisting of: alkyl moiety and aryl moiety, and R⁵, R⁶ are independently selected from the group consisting of: alkyl moiety, aryl moiety and arylamine moiety. Furthermore, R⁵ and R⁶ comprises one of the following groups:

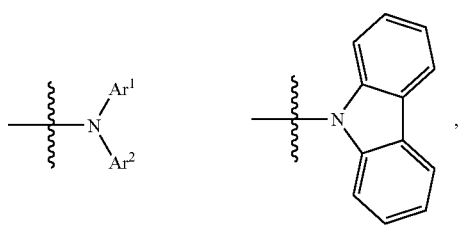

wherein Ar¹ and Ar² are identical or different, Ar¹ and Ar² are aryl moieties.

EXAMPLE 7

Synthesis of Compound 7

1,3-bis-(5-[1,10]phenanthroline-2-yl-[1,3,4]oxadiazol-2-yl)-benzene

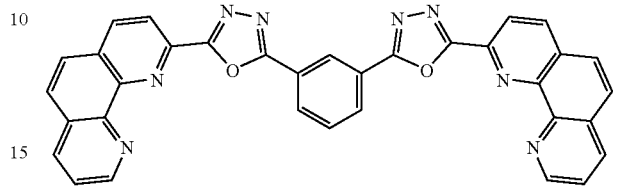

Step 1

Referring to scheme 7, a mixture of 30 g [1,10]phenanthroline, 26 g 30% hydrogen peroxide and 200 ml acetic acid was added to a flask, and the mixture was then heated to 50-60° C. and stirred overnight. After completion of reaction, the reaction mixture was cooled to room temperature, and vacuum distillated to remove acetic acid, and then 300 ml $CH_2Cl_2$ was added. Next, the solution was filtered to remove solids, and neutralized by adding $K_2CO_{3(aq)}$. The organic layer was separated, concentrated, and purified by column chromatography with silca gel (Methanol), so as to obtain solids [1,10]phenanthroline-N-oxide (23 g, yield 70.4%).

Step 2

23 g [1,10]phenanthroline-N-oxide and 37.5 g KCN were dissolved in 2.5 L water to form a mixture, and 65 g benzoyl chloride was added into the mixture drop by drop. Then, the mixture was stirred at room temperature overnight. After completion of reaction, solids were collected, purified by silica gel column (Hexane/$CH_2Cl_2$=1/2) and dried to obtain solids [1,10]phenanthroline-2-carbonitrile 6 g (yield 24.0%).

Step 3

To a flask was added a mixture of 6 g [1,10]phenanthroline-2-carbonitrile, 3.1 g $NH_4Cl$, 3.8 g $NaN_3$, 0.01 g LiCl and 60 ml DMF, and the mixture was then heated to 120-130° C. and stirred overnight. After completion of reaction, the reaction mixture was cooled to room temperature, filtered to remove solids, and vacuum distallated to remove DMF, and then 300 ml water was added. Next, $HCl_{(aq)}$ was added to adjust pH value to about 4, and stirred for 30 minutes. Finally, the solution was filtered to give solids, and then the solids were washed by water and dried to obtain products 2-(1H-tetrazol-5-yl)-[1,10]phenanthroline 6.1 g. (yield=84.0%).

Step 4: Similar to Step 4 in Example 1

Scheme 7

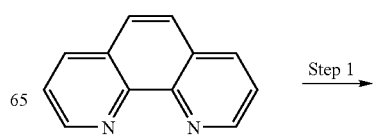

21
-continued

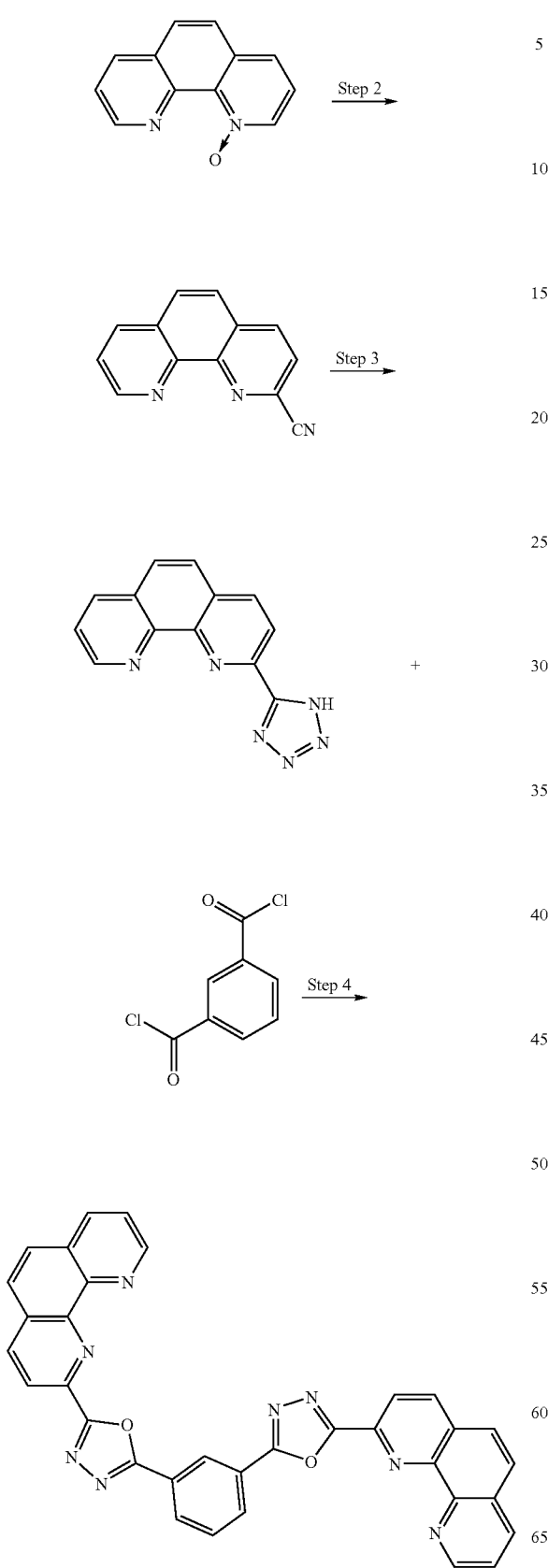

22

EXAMPLE 8

Synthesis of Compound 8

1,3,5-tris-(5-[1,10]phenanthroline-2-yl-[1,3,4]oxa-diazol-2-yl)-benzene

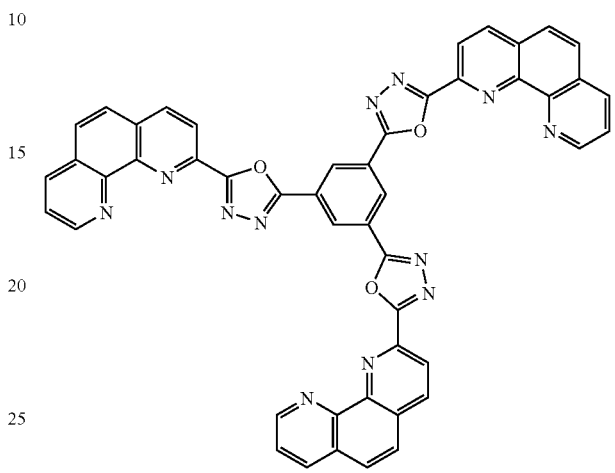

To a flask was added a mixture of 15 g 2-(1H-tetrazol-5-yl)-[1,10]phenanthroline and 300 ml pyridine. The mixture was then heated to 80-90° C., and 4.86 g 1,3,5 benzene tricarbonyl chloride was added. Subsequently, the mixture solution was heated to 110° C. and stirred overnight. After completion of reaction, as shown in scheme 8, the reaction mixture was filtered to collect solids. The solids was washed by pyridine and $CH_2Cl_2$ respectively, and then dried on oven to obtain products 6.6 g (yield=44.1%). MS(m/z, $FAB^+$), 888, 810, 521, 444, 155.

Scheme 8

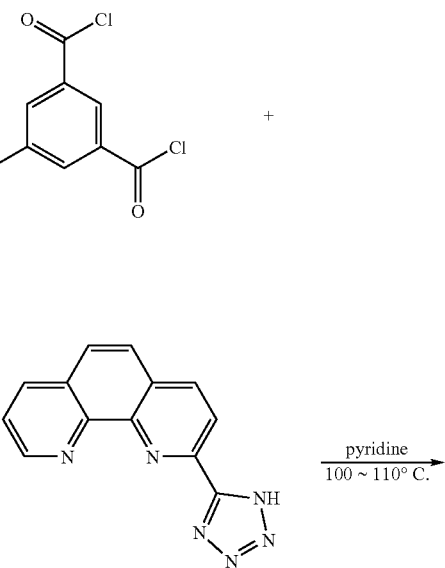

-continued

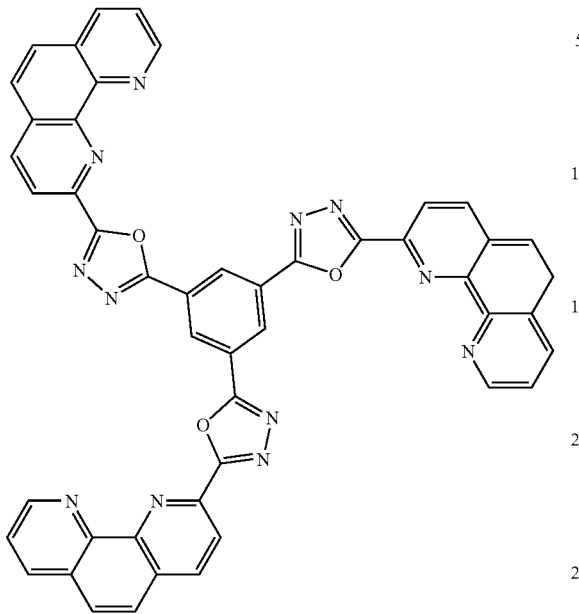

In a third embodiment of the present invention, a dipyridine-based compound which can be used as electron-transporting and/or hole blocking material or phosphorous host in organic electroluminescene devices is disclosed. The mentioned dipyridine-based compound is with a general formula as following:

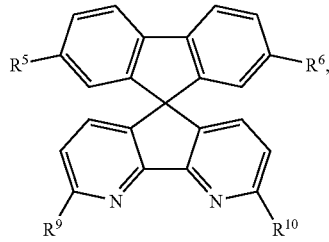

wherein $R^9$ and $R^{10}$ are identical or different, and $R^9$ and $R^{10}$ are independently selected from the group consisting of: hydrogen atom and

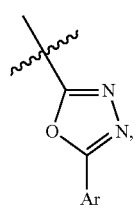

wherein Ar is aryl moiety: $R^5$ and $R^6$ are identical or different, and $R^5$ and $R^6$ comprises one of the following groups:

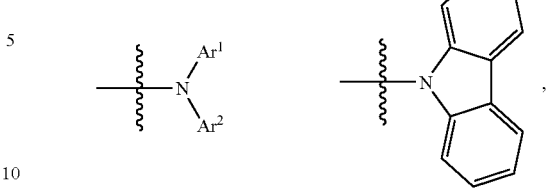

wherein $Ar^1$ and $Ar^2$ are identical or different, $Ar^1$ and $Ar^2$ are aryl moieties.

EXAMPLE 9

Synthesis of Compound 9

2,15-bis-[5-(4-tert-butyl-phenyl)-[1,3,4]oxadiazol-2-yl]-N,N,N,N-tetraphenyl-1,16-diaza-tetraphenylene-6-11-diamine

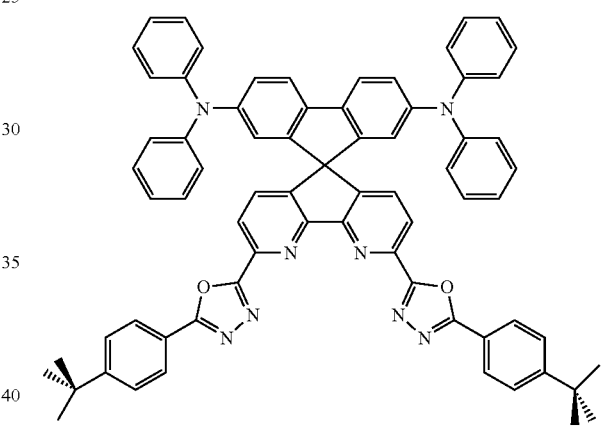

Step 1

Referring to scheme 9, a mixture of 3.53 g (5 mmole) 2,15-bis-[5-(4-tert-butyl-phenyl)-[1,3,4]oxadiazol-2-yl]-1,16-diaza-tetraphenylene, 160 ml $CH_2Cl_2$ and 0.01 g $FeCl_3$ was added to a 250 ml flask, and then a solution of 1.68 g bromine in 5 ml $CH_2Cl_2$ was added into the mixture drop by drop within 20 minutes. Next, the mixture solution was stirred at room temperature overnight. After completion of reaction, the reaction mixture was neutralized by adding $K_2CO_{3(aq)}$. The organic layer was separated, dehydrated by $MgSO_4$, vacuum concentrated, and purified by column chromatography, so as to obtain 6,11-Dibromo-2,15-bis-[5-(4-tert-butyl-phenyl)-[1,3,4]oxadiazol-2-yl]-1,16-diaza- teraphenylene (2.43 g, yield 56.25%).

Step 2

Under nitrogen atmosphere, a mixture of 2.43 g (2.8 mmole) 6,11-dibromo-2,15-bis-[5-(4-tert-butyl-phenyl)-[1,3,4]oxadiazol-2-yl]-1,16-diaza-teraphenylene, 1.43 g diphenylamine (8.4 mmole), 1.08 g sodium-tert-butoxide (11.3 mmole) 0.005 g $Pd(OAc)_2$ (0.02 mmole) and 120 ml o-xylene was added to a 250 ml flask. The mixture was then heated to reflux for 20 hours. After completion of reaction, the reaction was filtered to remove solids and placed into 600 ml methanol to give solids. The solids were collected and purified by column chromatography, so as to obtain 2,15-Bis-[5-(4-tert-butyl-phenyl)-[1,3,4]oxadiazol-2-yl]-N,N,N,N-tetraphenyl-1,16-diaza-tetraphenylene-6-11-diamine 1.2 g (yield=40.96%). MS(m/z, FAB+), 1053, 1052, 886; 317, 156, 105.

such as: resistively heated quartz boats. The thickness of the respective layer and the vapor deposition rate (0.1-0.3 nm/sec) are precisely monitored or set with the aid of a quartz-crystal monitor.

It is also possible, as described above, for individual layers to consist of more than one compound, i.e. in general a host material doped with a guest material. This is achieved by covaporization from two or more sources.

Tris-(8-hydroxyquinoline) aluminum ($Alq_3$) is most widely used as the electron transporting/light emitting layer in OLEDs for its high thermal stability and good film forming property. It is reported that the thermal degradation temperature ($T_d$) of $Alq_3$ is about 303° C.

A typical OLED consists of low work function metals, such as Al, Mg, Ca, Li and K, as the cathode by thermal evaporation, and the low work function metals can help

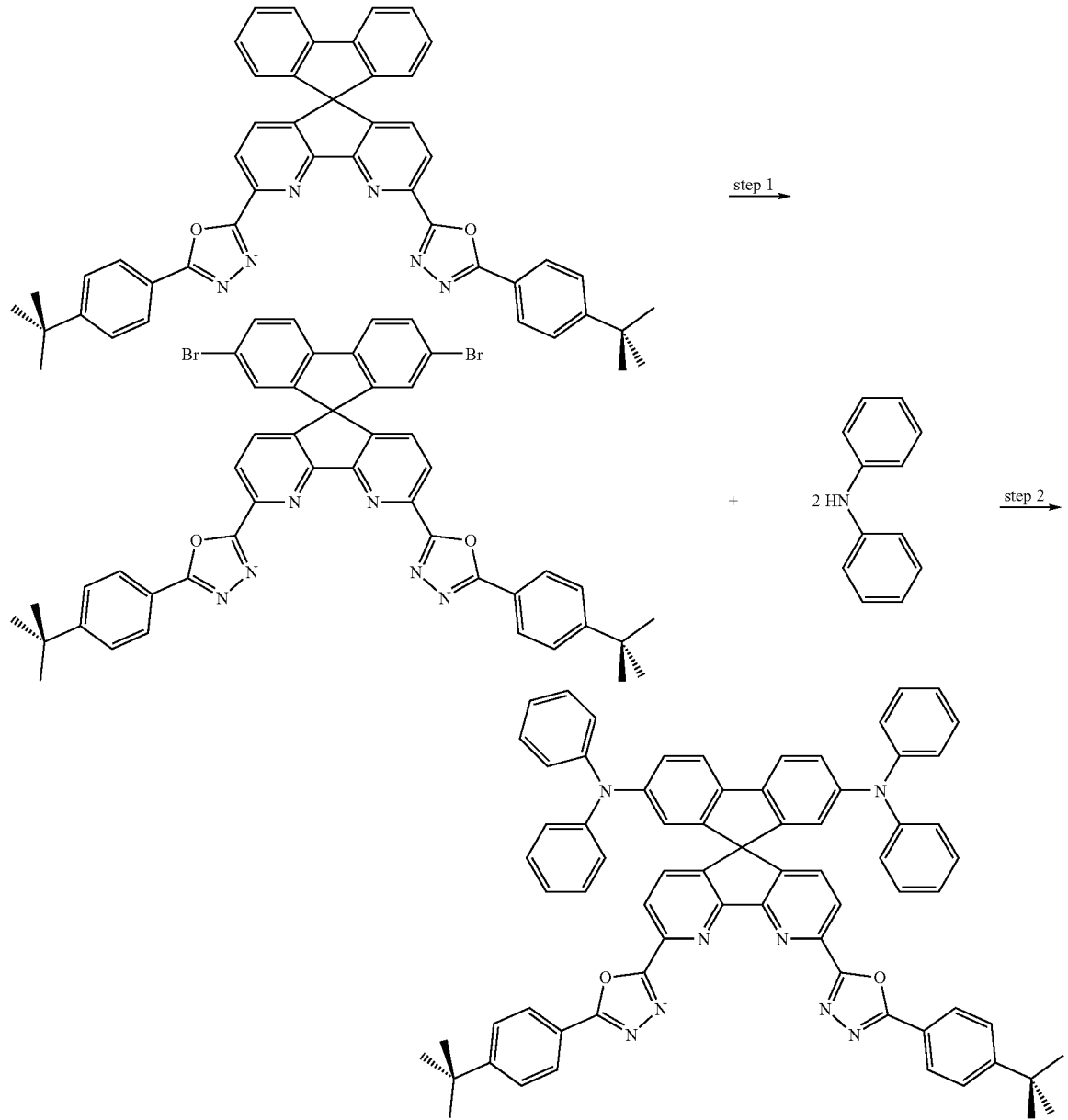

Scheme 9

GENERAL METHOD OF PRODUCING OLEDs

ITO-coated glasses with 15 $\Omega\square^{-1}$ and 1500 μm in thickness are provided (purchased from Sanyo vacuum, hereinafter ITO substrate) and cleaned in a number of cleaning steps in an ultrasonic bath (e.g. detergent, deionized water). Before vapor deposition of the organic layers, cleaned ITO substrates are further treated by UV and ozone.

The organic layers are applied onto the ITO substrate in order by vapor deposition in a high-vacuum unit ($10^{-6}$ Torr), electrons injecting the electron transporting layer from cathode. In addition, for reducing the electron injection barrier and improving the OLED performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the OLEDs are fabricated, EL spectra and CIE coordination are measured by using a PR650 spectra scan spectrometer. Furthermore, the current/voltage, luminescence/voltage and yield/voltage characteristics are taken with a Keithly 2400 programmable voltage-current source. The above-mentioned apparatuses are operated at room temperature (about 20° C.) and under atmospheric pressure.

EXAMPLE 10

Using a procedure analogous to the above mentioned general method, red-emitting OLEDs having the following structure were produced:

Device 1-1:
ITO/LT-N121(400 Å)/CBP doped 10% $Ir(piq)_2acac$(300 Å)/BCP(100 Å)/$Alq_3$(200 Å)/LiF(5 Å)/Al(1200 Å)

Device 1-2:
ITO/LT-N121(400 Å)/CBP doped 10% $Ir(piq)_2acac$(300 Å)/compound 2(100 Å)/$Alq_3$(200 Å)/LiF(5 Å)/Al(1200 Å)

Up to now, the molecular materials with hole-blocking ability are still very limited. Bathocuproine (BCP) has been widely used as an electron-transporting and hole-blocking material and has afforded high quantum efficiencies in organic EL devices based on iridium and platinum complexes. However, its morphological and thermal stability are poor. It is reported that BCP shows thermal degradation temperature ($T_d$) at about 268° C. In this example, BCP is used as hole-blacking layer in device 1-1, whereas the above-mentioned compound 2 is used as hole-blacking layer in device 1-2. The thermal properties of compound 2 is examined by thermogravimetric analysis (TGA) and differential scanning calorimetry (DSC), and it exhibits high thermal degradation temperature ($T_d$) at about 389° C. Additionally, LT-N121 is used as hole transport material in both devices 1-1 and 1-2, and its structure formula is as shown below. The LT-N121 is described in Example 6 of the previous application of the same applicant ("Conjugated compounds containing triarylamine structural elements, and their use", application number of United States application is 11/242,007, application date is 2005 Oct. 4)

Furthermore, 4,4'-bis(N-carbazolyl)biphenyl (CBP) is used as host material in both devices 1-1 and 1-2, and its structure formula is as shown below.

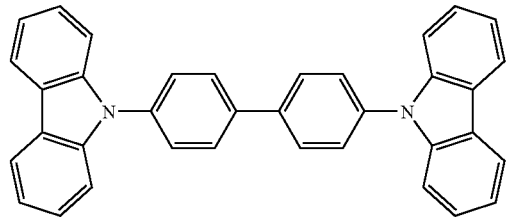

FIG. 1A shows voltage-current density characteristics of the devices. Both characteristics show the same trend, and current density is increased with increasing driving voltage. When driving voltages are the same, current density of device 1-2 is larger than that of device 1-1; in another word, when current densities are the same, driving voltage of device 1-2 is smaller than that of device 1-1. Therefore, device 1-2 shows higher circuit efficiency than BCP-based device 1-1.

Figure 1B:
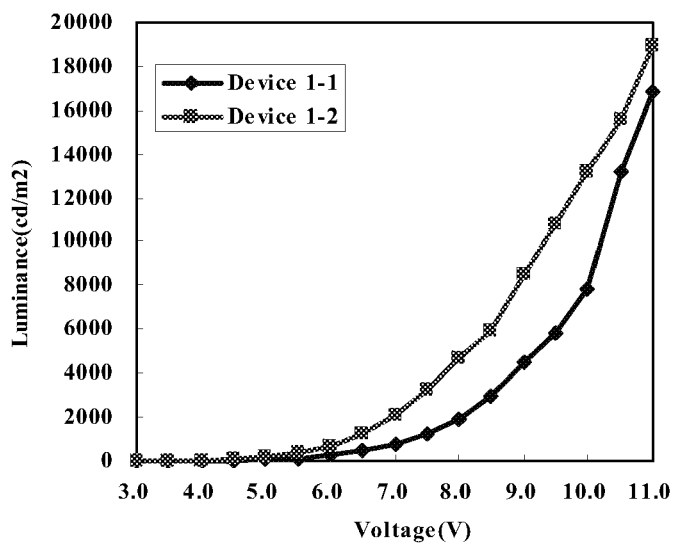
FIG. 1B shows plots of luminance v. voltage for device 1-1 and device 1-2.

Referring to FIG. 1B, luminance-voltage characteristics of device 1-1 and 1-2 show the same trend, and brightness is increased with increasing driving voltage. Device 1-2 exhibits larger brightness than that of device 1-1 at all driving voltage. Furthermore, the brightness of device 1-2 is about 13200 $cd/m^2$ at a driving voltage of 10V, while the brightness of BCP-based device 1-1 is 7810 $cd/m^2$.

Figure 1C:
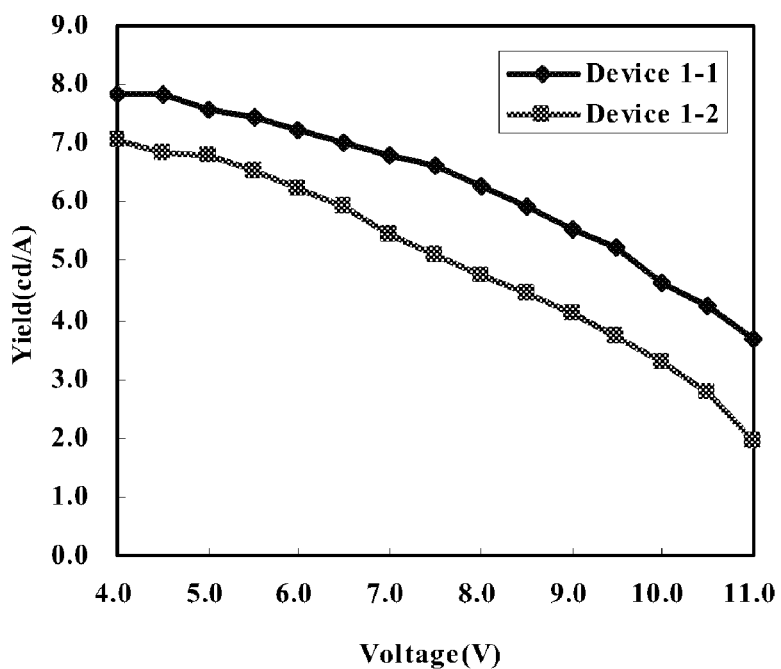
FIG. 1C shows plots of yield v. voltage for device 1-1 and device 1-2.

Referring to FIG. 1C, yield-voltage characteristics of device 1-1 and 1-2 show the same trend, and yield decreases with increasing voltage. Yield of device 1-1 is higher than that of device 1-2 at all voltage.

Figure 1D:
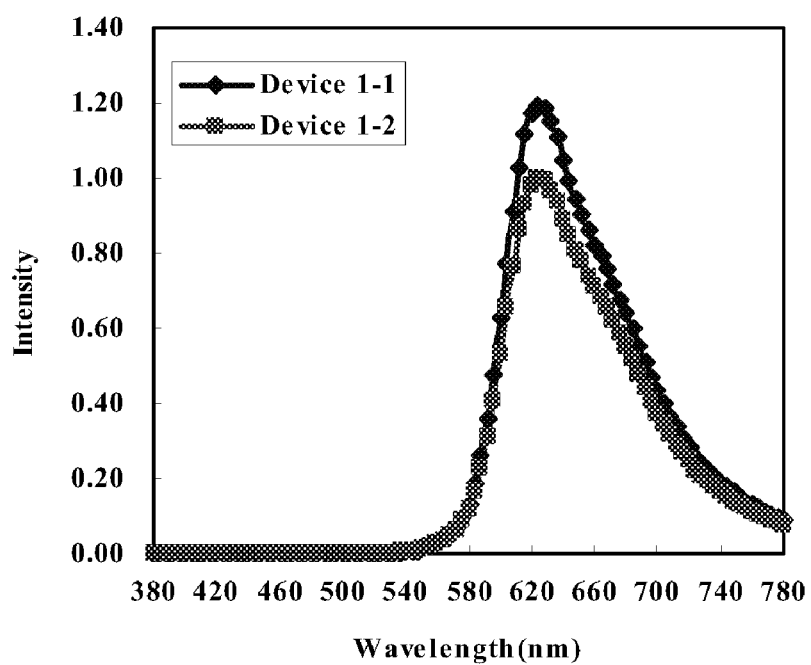
FIG. 1D shows plots of intensity v. wavelength for device 1-1 and 1-2.

As shown in FIG. 1D, device 1-2 provided in this invention allows fluorescent emission in the red spectral range, and has an emission maximum at 624 nm. This result is exactly the same with that of BCP-based device 1-1.

EXAMPLE 11

Using a procedure analogous to the above mentioned general method, green-emitting OLEDs having the following structure were produced:

Device 2-1:
ITO/NPB(500 Å)/$Alq_3$(600 Å)/LiF(5 Å)/Al(1200 Å)

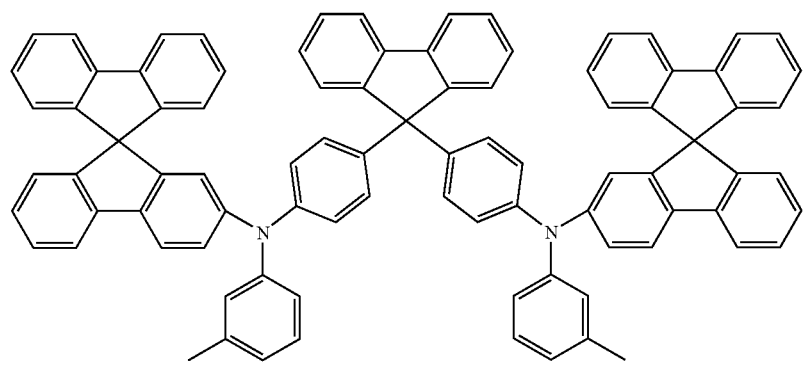

Device 2-2:

ITO/NPB(500 Å)/Alq$_3$(200 Å)/compound 8(400 Å)/LiF(5 Å)/Al(1200 Å)

In this example, Alq$_3$ is used as the electron transporting/light emitting layer in device 2-1, whereas the above-mentioned compound 8 is used as electron transporting layer in device 2-2. The thermal properties of compound 8 is examined by thermogravimetric analysis (TGA) and differential scanning calorimetry (DSC), and it exhibits high thermal degradation temperature (T$_d$) at about 381° C.

Figure 2A:
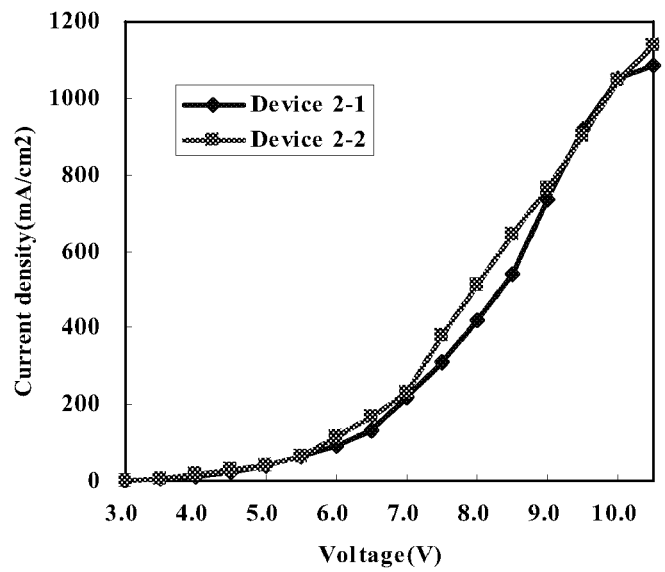
FIG. 2A shows plots of current density v. voltage for device 2-1 and device 2-2.

FIG. 2A shows voltage-current density characteristics of the devices. Both characteristics are similar and show the same trend, and current density is increased with increasing driving voltage. Therefore, circuitry efficiency of device 2-1 and 2-2 are close.

Figure 2B:
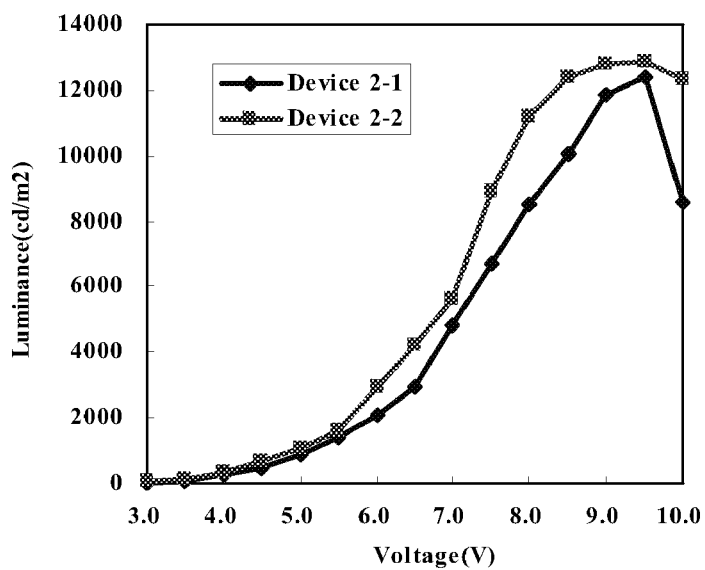
FIG. 2B shows plots of luminance v. voltage for device 2-1 and device 2-2.

Referring to FIG. 2B, when driving voltage is lower than 9.5 V, luminance-voltage characteristics of device 2-1 and 2-2 show the same trend, and brightness is increased with increasing driving voltage. Device 2-2 exhibits larger brightness than that of device 2-1 at all driving voltage. Furthermore, when driving voltage is higher than 9.5 V, brightness of device 2-1 slightly decreases, while brightness of device 2-1 decreases dramatically.

Figure 2C:
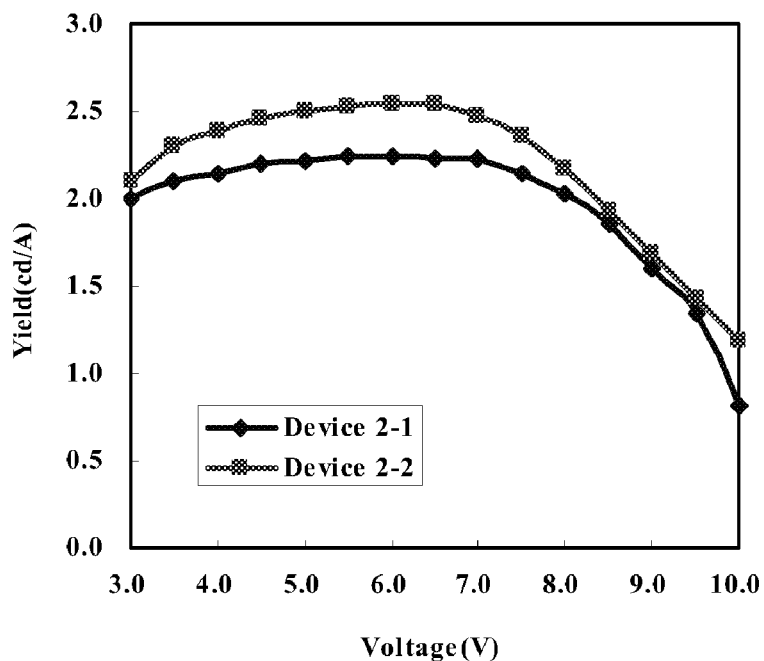
FIG. 2C shows plots of yield v. voltage for device 2-1 and device 2-2.
Figure 2D:
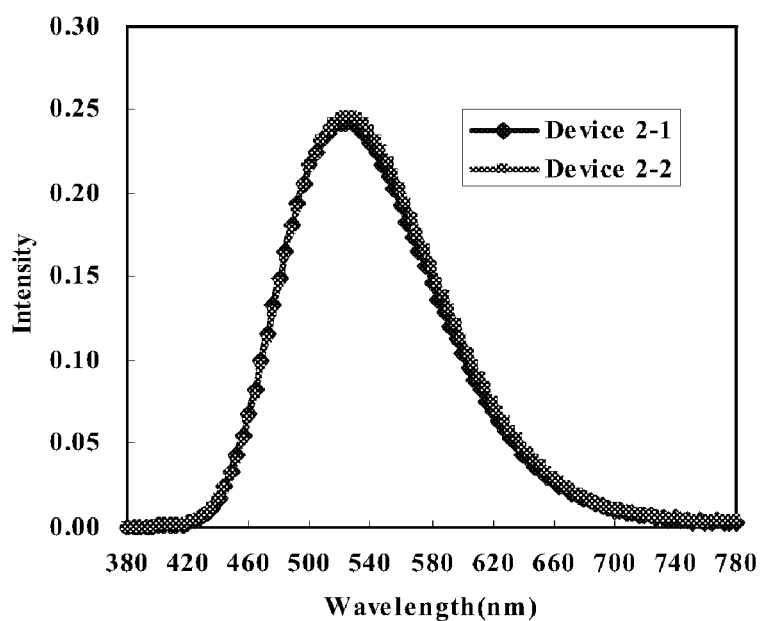
FIG. 2D shows plots of intensity v. wavelength for device 2-1 and 2-2.

Referring to FIG. 2C, yield-voltage characteristics of device 2-1 and 2-2 show the same trend, and yield decreases with increasing voltage. Yield of device 2-2 is higher than that of device 2-1 at all voltage. Moreover, when voltage is higher than 8 V, yields of both devices are similar.

As shown in FIG. 1D, device 2-2 provided in this invention allows fluorescent emission in the green spectral range, and has an emission maximum at about 524-528 nm. This result is very close to that of device 2-1, wherein device 2-1 exhibits an emission maximum at about 520-528 nm.

EXAMPLE 12

Using a procedure analogous to the above mentioned general method, red-emitting OLED having the following structure was produced:

Device 3:

ITO/LT-N121(400 Å)/compound 5 doped 15% Ir(piq)$_2$(acac)(300 Å)/BCP(80 Å)/Alq$_3$(200 Å)/LiF(5 Å)/Al(1200 Å)

In this example, BCP is used as hole-blacking layer in device 3, whereas the above-mentioned compound 5 is used as phosphorous host. Additionally, LT-N121 is used as hole transport material in device 3.

Figure 3A:
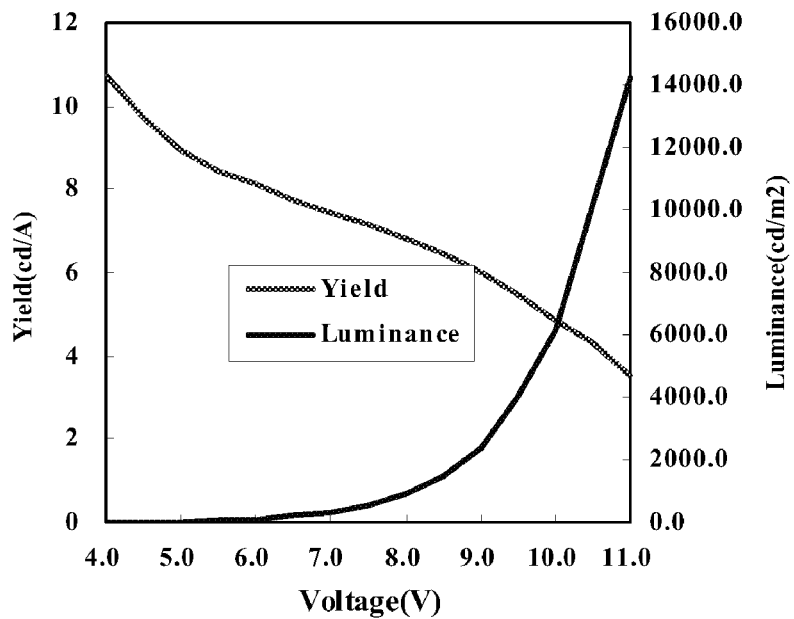
FIG. 3A shows plots of luminance v. voltage for device 3, and plots of yield v. voltage for device 3.

Referring to FIG. 3A, yield of device 3 remains in high level at all driving voltage. For example, when driving voltage approaches to 10V, yield of device 3 decreases to about 5 cd/A.

Figure 3B:
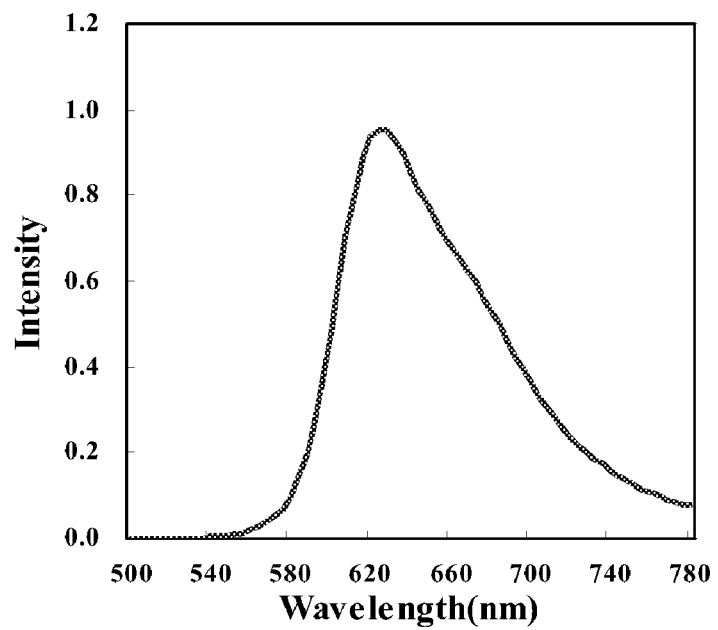
FIG. 3B shows plots of intensity v. wavelength for device 3.

As shown in FIG. 3B, device 3 provided in this invention allows fluorescent emission in the red spectral range, and has an emission maximum at 624 nm. This result is exactly the same with that of BCP-based device 1-1.

In the above preferred embodiments, we show that dipyridine-based compounds have efficient electron transporting and hole-blocking properties with high thermal stability and practical operation durability. Good performance has also been achieved using the mentioned dipyridine-based compounds for red- and green-emitting organic electroluminescent devices.

To sum up, the present invention discloses a dipyridine-based compound which can be used as electron-transporting and/or hole blocking material or phosphorous host in organic electroluminescence devices is disclosed. The mentioned dipyridine-based compound is represented by the following formula:

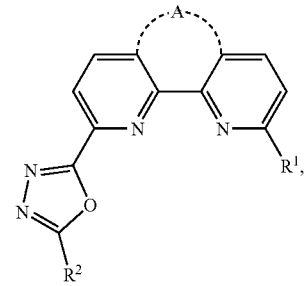

wherein R$^1$ and R$^2$ are identical or different, and R$^1$ and R$^2$ are independently selected from the group consisting of: hydrogen atom, aryl moiety, hetero cycle, multiple fused ring, multiple fused ring with hetero atom(s); A is selected from the following group:

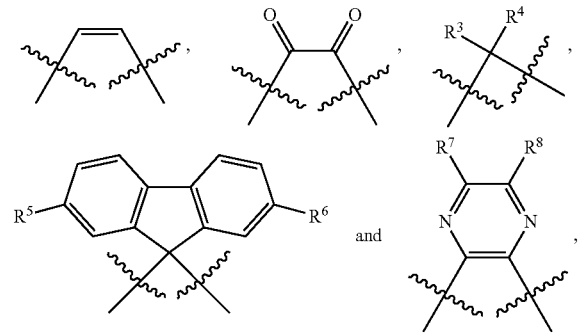

wherein R$^3$ and R$^4$ are identical or different, R$^5$ and R$^6$ are identical or different, R$^7$ and R$^8$ are identical or different, R$^3$, R$^4$, R$^7$, R$^8$ are independently selected from the group consisting of: alkyl moiety and aryl moiety, and R$^5$, R$^6$ are independently selected from the group consisting of: alkyl moiety, aryl moiety and arylamine moiety.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A dipyridine-based compound with a general formula as following:

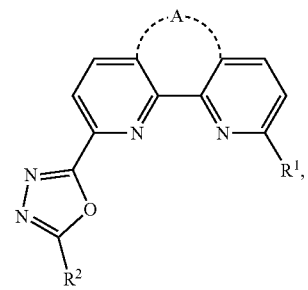

wherein $R^1$ and $R^2$ are identical or different, and $R^1$ and $R^2$ are independently selected from the group consisting of: hydrogen atom, aryl group, pyridine group, and oxadiazole group, A is selected from the following group:

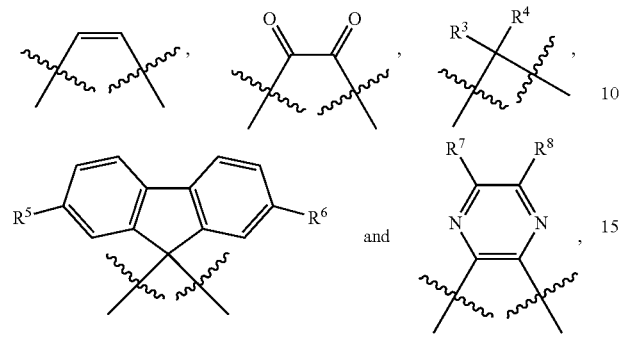

wherein $R^3$ and $R^4$ are identical or different, $R^5$ and $R^6$ are identical or different, $R^7$ and $R^8$ are identical or different, $R^3$, $R^4$, $R^7$, $R^8$ are independently selected from the group consisting of: alkyl group and aryl group, and $R^5$, $R^6$ are independently selected from the group consisting of: alkyl group, aryl group and arylamine group.

2. The compound as claimed in claim 1, wherein $R^1$ represents one of the following groups:

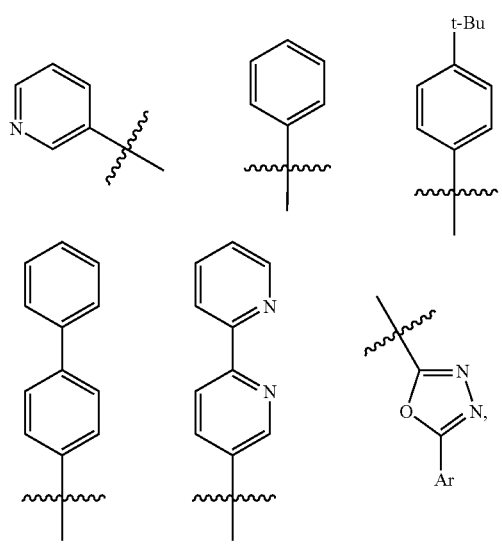

wherein Ar is aryl group.

3. The compound as claimed in claim 1, wherein $R^2$ represents one of the following groups:

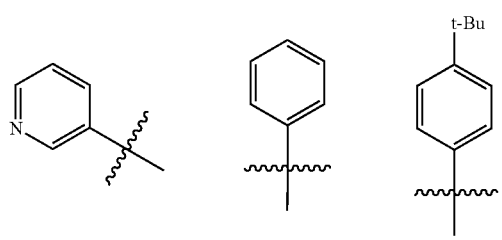

-continued

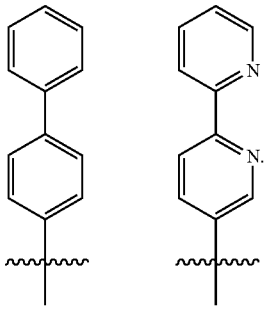

4. The compound as claimed in claim 1, wherein $R^5$ and $R^6$ represents one of the following groups:

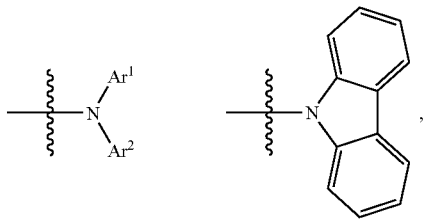

wherein $Ar^1$ and $Ar^2$ are identical or different, $Ar^1$ and $Ar^2$ are aryl groups.

5. An electroluminescence device comprising one or more active layers, wherein at least one of these active layers comprises the compound as claimed in claim 1 as electron-transporting material, and said electron-transporting material is between an electroluminescence layer and a cathode.

6. An electroluminescence device comprising one or more active layers, wherein at least one of these active layers comprises the compound as claimed in claim 1 as hole blocking material, and said hole blocking material is between an electroluminescence layer and a cathode.

7. An electroluminescence device comprising one or more active layers, wherein at least one of these active layers comprises the compound as claimed in claim 1 as phosphorous host material, and said phosphorous host material is between a cathode and an anode.

8. A dipyridine-based compound with a general formula as following:

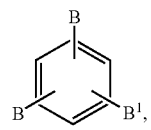

wherein $B^1=B$ or hydrogen atom, and the structure of B is as following:

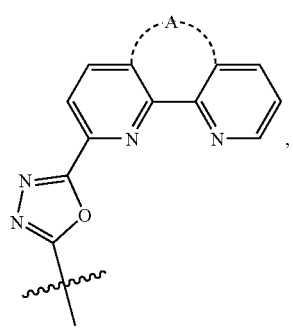

wherein A is selected from the following group:

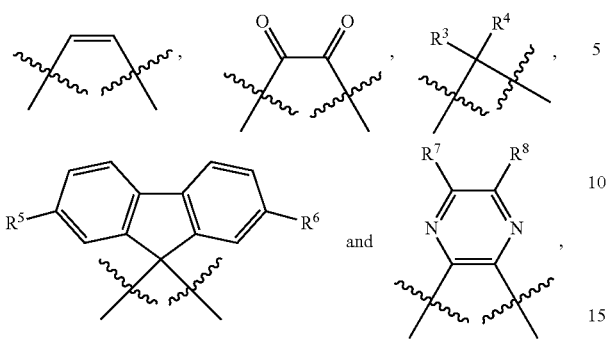

wherein $R^3$ and $R^4$ are identical or different, $R^5$ and $R^6$ are identical or different, $R^7$ and $R^8$ are identical or different, $R^3$, $R^4$, $R^7$, $R^8$ are independently selected from the group consisting of: alkyl group and aryl group, and $R^5$, $R^6$ are independently selected from the group consisting of: alkyl group, aryl group and arylamine group.

9. The compound as claimed in claim 8, wherein $R^5$ and $R^6$ represents one of the following groups:

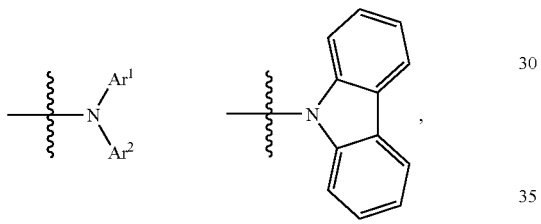

wherein $Ar^1$ and $Ar^2$ are identical or different, $Ar^1$ and $Ar^2$ are aryl moieties.

10. The compound as claimed in claim 8, wherein the chemical structure of the dipyridine-based compound is as following:

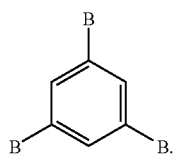

11. An electroluminenscence device comprising one or more active layers, wherein at least one of these active layers comprises the compound as claimed in claim 8 as electron-transporting material, and said electron-transporting material is between an electroluminescence layer and a cathode.

12. An electroluminescence device comprising one or more active layers, wherein at least one of these active layers comprises the compound as claimed in claim 8 as hole blocking material, and said hole blocking material is between an electroluminescence layer and a cathode.

13. An electroluminescence device comprising one or more active layers, wherein at least one of these active layers comprises the compound as claimed in claim 8 as phosphorous host material, and said phosphorous host material is between a cathode and an anode.

14. A dipyridine-based compound with a general formula as following:

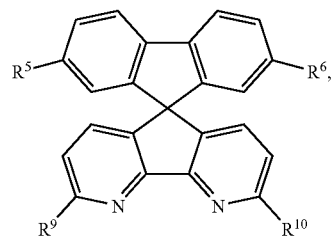

wherein $R^9$ and $R^{10}$ are identical or different, and $R^9$ and $R^{10}$ are independently selected from the group consisting of: hydrogen atom and

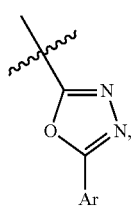

wherein Ar is aryl group, at least one of $R^9$ and $R^{10}$ represents

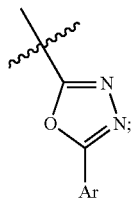

$R^5$ and $R^6$ are identical or different, and $R^5$ and $R^6$ represents one of the following groups:

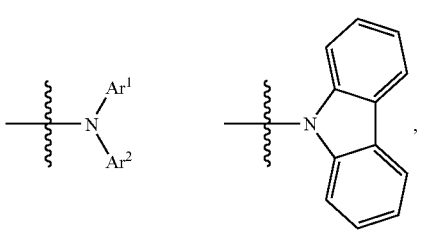

wherein $Ar^1$ and $Ar^2$ are identical or different, $Ar^1$ and $Ar^2$ are aryl groups.

15. An electroluminenscence device comprising one or more active layers, wherein at least one of these active layers comprises the compound as claimed in claim 14 as electron-transporting material, and said electron-transporting material is between an electroluminescence layer and a cathode.

16. An electroluminescence device comprising one or more active layers, wherein at least one of these active layers comprises the compound as claimed in claim 14 as hole blocking material, and said hole blocking material is between an electroluminescence layer and a cathode.

17. An electroluminescence device comprising one or more active layers, wherein at least one of these active layers comprises the compound as claimed in claim 14 as phosphorous host material, and said phosphorous host material is between a cathode and an anode.

* * * * *